US009140544B2

(12) United States Patent
Barak et al.

(10) Patent No.: US 9,140,544 B2
(45) Date of Patent: Sep. 22, 2015

(54) OPTICAL SYSTEM AND METHOD FOR MEASURING IN PATTERNED STRUCTURES

(75) Inventors: Gilad Barak, Rehovot (IL); Boaz Brill, Rehovot (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 63 days.

(21) Appl. No.: 14/233,466

(22) PCT Filed: Jul. 18, 2012

(86) PCT No.: PCT/IL2012/050253
§ 371 (c)(1),
(2), (4) Date: Jan. 17, 2014

(87) PCT Pub. No.: WO2013/011508
PCT Pub. Date: Jan. 24, 2013

(65) Prior Publication Data
US 2014/0168646 A1    Jun. 19, 2014

Related U.S. Application Data

(60) Provisional application No. 61/509,127, filed on Jul. 19, 2011.

(51) Int. Cl.
| | |
|---|---|
| G01N 21/00 | (2006.01) |
| G01B 11/22 | (2006.01) |
| G01B 11/24 | (2006.01) |
| G03F 7/20 | (2006.01) |
| G01N 21/27 | (2006.01) |
| G01N 21/95 | (2006.01) |
| H01L 21/66 | (2006.01) |

(52) U.S. Cl.
CPC ................ *G01B 11/22* (2013.01); *G01B 11/24* (2013.01); *G01N 21/27* (2013.01); *G01N 21/9501* (2013.01); *G03F 7/70625* (2013.01); *H01L 22/12* (2013.01); *H01L 2924/0002* (2013.01)

(58) Field of Classification Search
CPC ... H01J 37/32935; G01N 21/64; G01N 21/68; G01N 2015/1037; G01J 3/02
USPC .............. 356/300–326, 237.1, 370, 625, 402, 356/72–73
See application file for complete search history.

(56) References Cited

U.S. PATENT DOCUMENTS

| | | |
|---|---|---|
| 5,087,121 A | 2/1992 | Kakuchi et al. |
| 6,690,469 B1 | 2/2004 | Shibata et al. |

(Continued)

OTHER PUBLICATIONS

International Search Report for Appln. No. PCT/IL2012/050253 mailed Nov. 16, 2012.

*Primary Examiner* — Abdullahi Nur
(74) *Attorney, Agent, or Firm* — Browdy and Neimark, PLLC

(57) ABSTRACT

An optical system is presented for use in measuring in patterned structures having vias. The optical system comprises an illumination channel for propagating illuminated light onto the structure being measured; a detection channel for collecting light returned from the illuminated structure to a detection unit; and an attenuation assembly accommodated in the illumination and detection channels and being configured and operable for selectively attenuating light propagating along the detection channel, the attenuation creating a predetermined condition for the selectively attenuated light, said predetermined condition being defined by a predetermined ratio between a first light portion corresponding to a dark field condition and a second light portion corresponding to a bright field condition in said selectively attenuated light, detected selectively attenuated light being therefore indicative of at least one parameter of the via being illuminated.

27 Claims, 7 Drawing Sheets

(56) References Cited

U.S. PATENT DOCUMENTS 6,768,543 B1 * 7/2004 Aiyer ................. 356/237.4
7,295,303 B1 11/2007 Vaez-Iravani et al.
2010/0284027 A1 11/2010 Scheiner
2011/0172974 A1 7/2011 Ku et al.

* cited by examiner

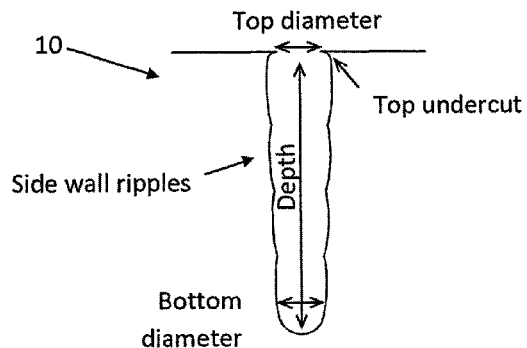
FIG. 1 (GENERAL ART)
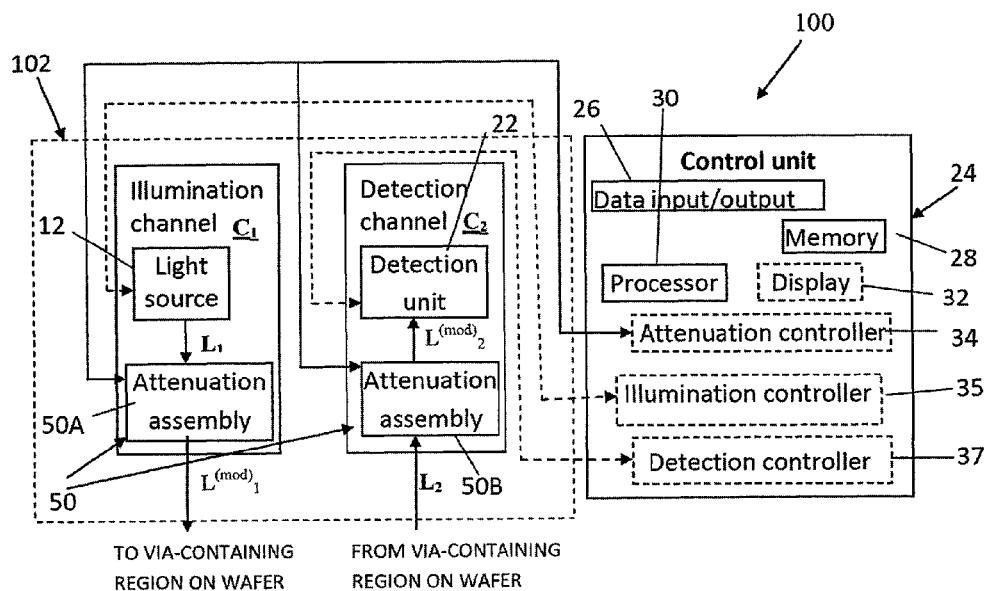
FIG. 2

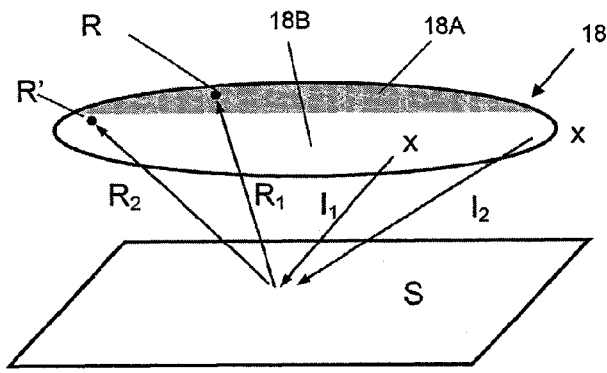
FIG. 5A
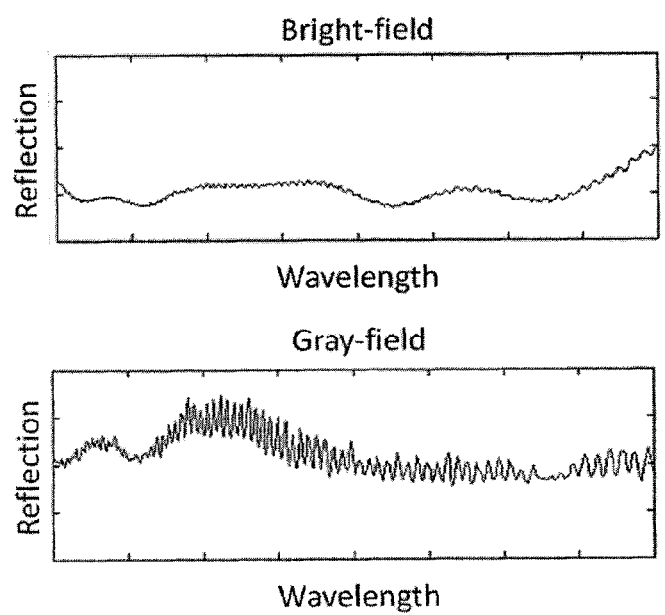
FIG. 5B
FIG. 5C

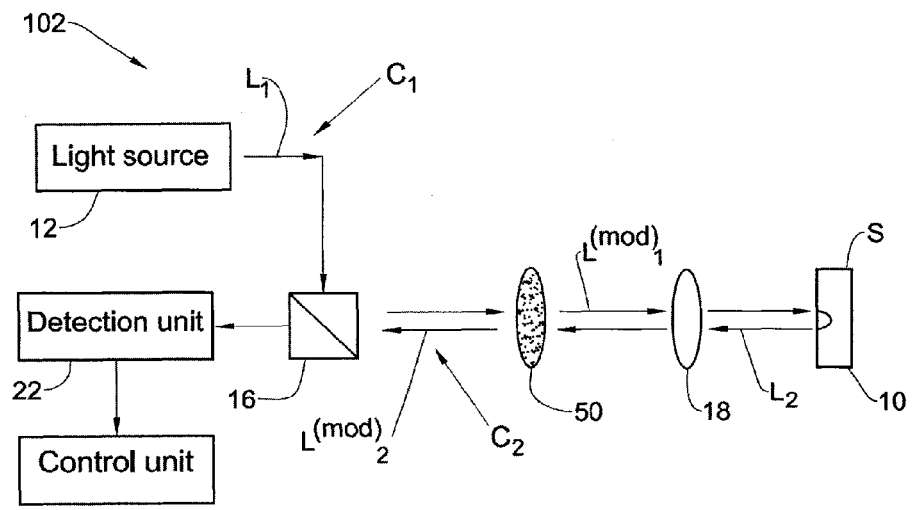
FIG. 6A
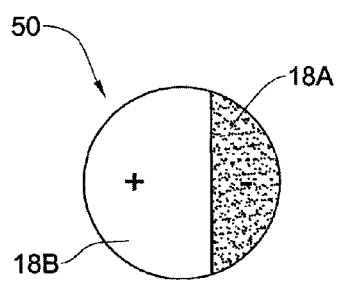
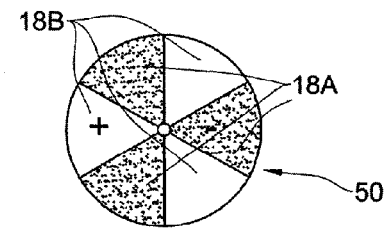
FIG. 6B  FIG. 6C

OPTICAL SYSTEM AND METHOD FOR MEASURING IN PATTERNED STRUCTURES

TECHNOLOGICAL FIELD

The present invention is generally in the field of optical measurement techniques, and relates to an optical system and method for measuring in patterned structures, such as semiconductor wafers having vias.

BACKGROUND

As semiconductor technology progresses, shrinking device dimensions has become an increasingly complex task. One approach to overcome these difficulties is by using vertical integration of multiple semiconductor devices (chips). This allows larger number of devices per unit (e.g. in memory applications), as well as integration of chips of different functionality thus allowing better performance of a hybrid system (e.g. sensor, processor and memory).

One method under development for vertical integration is based on Through Silicon Via (TSV). TSV is a vertical electrical connection (via) passing completely through a silicon wafer or die. TSV is a high performance technique to create 3D packages and 3D integrated circuits (as compared to its alternatives such as package-on-package), because the density of vias is substantially higher and the length of the connections is shorter. According to TSV, conducting pillars are formed within a silicon substrate, later to be used for contacting successive chips. To connect electrically the components in different layers, TSV technology is used to provide the electrical interconnect and to provide mechanical support. In TSV technology, a via is fabricated in a silicon chip with different active integrated circuit devices or other devices fabricated by a semiconductor process, and the via is filled with metal such as Cu, Au, W, solders, or a highly-doped semiconductor material such as polysilicon. Multiple components provided with such vias are then stacked and bonded together.

One critical step in the TSV process is via formation, in which a pattern of contacts is etched into the silicon. In order to maintain the required via quality, it is essential to control both the depth and profile of the vias.

GENERAL DESCRIPTION

There is a need in the art for a novel technique for monitoring parameters of pattern features produced during a TSV fabrication process, in particular monitoring the depth of vias being created.

TSV are created by deep silicon etch, yielding a vertical hole in the silicon with high aspect ratio. TSV can have different cross sections, depending on the specific intended application and integration scheme, and can have circular, square, octagonal or annular shapes. Vias actually present narrow grooves, namely high aspect ratio grooves, i.e. high ratio between the via depth (height) and width (cross sectional dimension). Typical cross section sizes of the via (via diameters) are in the range of 1-50 µm, and depths are up to 200 µm, providing aspect ratios up to 20:1. Etching is followed by placing a thin insulating layer (called a 'liner') inside the via, which step is in turn followed by growth of another layer ('barrier') that limits the diffusion of Cu atoms, and then by the growth of a thin metallic layer, called a 'seed', intended to improve the deposition process of the copper, making up the contact. Characterization of all these thin layers is also of great industrial interest, as small defects, inhomogeneities and gaps can impair the TSV functionality.

To ensure reliable and repeatable integration process, several crucial via profile parameters require monitoring and control such parameters as the via depth, top diameter, sidewall angle, side wall ripples (i.e. an oscillatory indent pattern appearing on the via walls as a result of the TSV fabrication process), bottom diameter and top undercut. In this connection, reference is made to FIG. 1 schematically illustrating a via profile 10.

As shown, the via 10 is typically defined by its top diameter, bottom diameter, depth, and sidewall ripples, see above. The via depth should exceed the final planned thickness of the layer in the chip stack, so that after thinning the wafer, it will form a connection between the two sides of the chip. The sidewall ripples should be reduced as much as possible to provide a substantially smooth side wall profile. "Smooth" via's side walls are required to ensure optimal filling of the via. The top and bottom diameters usually define a side wall angle. The coating and filling processes of the TSV, in following fabrication steps, require side walls of well-controlled angle. In addition, in order to guarantee good conductive properties of interconnect, significant bottom diameters must be maintained. In other words, the side-wall slope is needed to be kept very close to vertical. A possible consequence of the etching process is the creation of an undercut at the top edge of the via (top undercut). Such undercut may impair the following filling process. Additional parameters of interest relate to coating or other processes done following the formation of the via which form thin layers on the via wall. In all cases, there is a need in the industry to control the thickness of these layers, hence to measure them.

Generally, the via top-diameter can be determined using several known techniques, including for example bright-field optical imaging, in which light is normally incident on the via region and specularly reflected light is detected and analyzed. However, such normal-incidence bright-field imaging cannot be used for information on the via depth for vias, especially vias with large aspect ratios which is typical for TSV. Other common approaches that have been suggested for the via depth determination are based on interferometric methods.

As the via top-diameter is decreased, an optical signal reaching the via bottom is reduced leading to significant difficulty in measurement of deep and narrow vias. Further, when measuring in structures with small via top-diameter, an illuminated spot is typically larger than the top-diameter and thus light detected with bright-field mode is mainly contributed by light reflected from the top surface of the structure outside the via, thus even more reducing the effective detection from the bottom of the via. In this connection, the following should be noted.

One possible approach for measuring the via depth is through spectral-reflectometry. In this method, light is focused on the via area, typically from the top (i.e. normal incidence mode), and is reflected from both the via bottom and the wafer top surface. Alternatively, IR light (in the wavelength range where Si is transparent) can be incident on the wafer from below, and the light reflected from the via bottom and the wafer surface is measured.

The interference signal/pattern between light reflected from the via bottom and light reflected from the wafer surface can be expressed as fast oscillations in the spectral response:

$$A(k) \approx A_0(k) + A_1(k)\cos(2Dk)$$

where A is the reflected spectrum, $k=2\pi/\lambda$ is the light wavenumber, $A_0$ and $A_1$ are slow-varying functions of k, primarily determined by the reflection intensity from the interfaces, and D is the via depth. As shown in Eq. 1, the spectral oscillations have a specific periodicity in k, given by 2D. This relation is applicable for wide vias, while for vias of typical diameter comparable or smaller than the used wavelength it should be modified, as will be explained below.

The inventors have found that one of the difficulties in the use of spectral-reflectometry method for measuring in structures with high aspect ratio vias (which are required in high-end semiconductor devices) is associated with the different intensities of light reflected from the via bottom and light reflected from the wafer surface. Generally speaking, the amplitude of the fast oscillations arising from the via is determined by the amount of light reflected from the via bottom into the detector. In contrast, the measured noise is determined by the entire measured signal, predominantly determined by the reflection from the wafer surface. The small ratio between these two values limits the ability to measure the depth of high aspect ratio vias.

Also, the inventors have found that the use of dark field detection mode in the spectral-reflectometry while enabling determination of the profile of via side walls, might not provide sufficient information about the via depth. This is because pure dark field detection mode actually filters out a specular reflection component in light returned from the via bottom and the wafer surface. The via bottom is not "flat", i.e. is not entirely parallel to the wafer surface, but rather is curved and light response of the via bottom to incident light is thus formed by both specular reflection and scattering components.

The technique of the present invention is based on the use of a novel, so-called "gray-field" measurement approach, aimed at appropriately modifying a relation between the above two factors, namely specular reflection and scattered components in the detected signal. This approach makes use of the above mentioned fact that the via bottom is not "flat", which provides that light reflected/returned from the via bottom has both its direction and its polarization different with respect to those of the incident light and accordingly of the light specularly reflected from the wafer surface which maintains the direction and polarization of the incident light.

The gray field measurement technique of the present invention utilizes selective attenuation of specular reflection component of a light response the illuminated via-including region of the structure (wafer), where such attenuation creates a gray-field detection condition presenting a predetermined combined dark and bright field detection condition for the light response signal. This combined dark and bright field detection condition is such that the selectively attenuated light comprising light specularly reflected from a wafer surface and from via bottom and light scattered from the via bottom and side walls of the via, includes a first light portion formed by scattered light and a second light portion formed by specular reflections, with a predetermined ratio between the intensities of the first and second light portions.

Measured data is in the form of a spectral signature formed by detection of the selectively attenuated light. Such spectral signature when corresponding to a required ratio between the dark and bright light response component, provides for proper analysis of the measured data for determining data indicative of at least one parameter of the via being illuminated, in particular the via depth. Such analysis may include spectral analysis based on identifying in the spectral signature frequencies characterizing the light response of the via bottom thus enabling extraction of the light response of the side walls of the via.

It should be noted that the measurement technique of the present invention can be implemented either for an isolated structure or a lattice of similar elements.

Thus, according to one broad aspect of the invention, there is provided an optical system for use in measuring in patterned structures having vias, the system comprising: an illumination channel for propagating illuminated light onto the structure being measured, a detection channel for collecting light returned from the illuminated structure to a detection unit, and an attenuation assembly accommodated in the illumination and detection channels and being configured and operable for selectively attenuating light propagating along the detection channel, the attenuation creating a predetermined condition for the selectively attenuated light, said predetermined condition being defined by a predetermined ratio between a first light portion corresponding to a dark field condition and a second light portion corresponding to a bright field condition in said selectively attenuated light, detected selectively attenuated light being therefore indicative of at least one parameter of the via being illuminated.

As indicated above, the first and second light portions correspond to respectively substantially scattered light and substantially specularly reflected light.

Preferably, the illuminating channel comprises a broadband light source, and the detection channel comprises a spectrometer, the detected light being in the form of a spectral signature. The spectral signature is indicative of at least a depth of the via being illuminated.

Also, preferably, the illumination and detection channels are configured in accordance with a normal incidence mode.

In some embodiments, the attenuating assembly is configured and operable for affecting at least polarization of light passing along the illumination and detection channels. For example, the attenuating assembly comprises first and second polarizers accommodated in the illumination and detection channels and having planes of polarization forming a predetermined acute angle between them. The acute angle is preferably closer to 90 degrees, for example higher than 70 degrees. The predetermined acute angle is selected such that intensities of the first and second light portions are of the same order.

The attenuating assembly may comprise first and second polarizers accommodated in the illumination and detection channels respectively and having planes of polarization oriented to form said predetermined acute angle, and a common phase retarder accommodated in the illumination and detection channels, and being located upstream of the second polarizer with respect to a direction of propagation of light returned from the structure along the detection channel.

In another possible example, the attenuating assembly may comprise a common polarizer and a common phase retarder both accommodated in a spaced-apart relationship in a common portion of the illumination and detection channels. The polarizer is located upstream of the phase retarder with respect to a direction of propagation of the illuminating light to the structure along the illumination channel.

In some embodiments of the invention, the attenuating assembly is configured and operable for partial masking of both the illumination and detection channels. The attenuating assembly may comprise a mask with a predetermined transmission pattern, configured to provide the predetermined ratio between the intensities of the first and second light portions. The mask may be located in a plane intersecting the illumination and detection channels. In an alternative example, the attenuating assembly may comprise first and second masks having complementary patterns, each pattern being formed by regions of different light transmission with respect to the first and second light portions.

The mask has two or more segments of different transmissions with respect to the first and second light portions.

The optical system may be associated with (connectable to) a control unit configured and operable for receiving measured data (e.g. spectral signature) indicative of the selectively attenuated light in the detection channel, and processing said measured data to determine at least one parameter of the via.

The optical system may be associated with/connectable to a control unit configured and operable for selectively operating the attenuating assembly for selectively shifting it into an operative mode corresponding to the predetermined combined dark and bright field detection condition. The control unit may be configured and operable to further operate the attenuating assembly in either one of the following additional modes: a bright field detection mode, a dark field detection mode, and intermediate mixed dark and bright field detection modes.

According to another broad aspect of the invention, there is provided a method for use in optical measurements in patterned structures having vias, the method comprising selectively attenuating light returned from an illuminated via-including region, the attenuation creating a predetermined combined dark and bright field detection condition such that said selectively attenuated returned light comprises a first light portion corresponding to a dark field condition and a second light portion corresponding to a bright field condition, with a predetermined ratio between intensities of the first and second light portions, the selectively attenuated returned light being therefore indicative of at least one parameter of the via being illuminated.

According to yet further aspect of the invention, there is provided a method for use in optical measurements in patterned structures having vias, the method comprising: providing an optical system configured and operable for performing optical measurements with a bright field detection mode and a dark field detection mode, and selectively operating said optical system for applying an attenuation mode for selectively attenuating light returned from an illuminated via-including region, to thereby create a predetermined combined dark and bright field detection condition for said attenuated returned light, such that the attenuated returned light comprises a first light portion corresponding to a dark field condition and a second light portion corresponding to a bright field condition, with a predetermined ratio between intensities of the first and second light portions, the attenuated returned light being therefore indicative of at least one parameter of the via being illuminated.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 schematically illustrates a typical via sectional view showing such parameters as top diameter, bottom diameter, depth, and sidewall ripples;

FIG. 2 is a block diagram of a measurement system according to the invention configured and operable for performing gray-field detection mode;

FIGS. 5A to 5C illustrate the principles of another embodiments of the invention utilizing masking effects in the attenuating assembly of the optical system of the invention, where FIG. 5A shows the principles of masking effect on light interacting with the mask pattern, and FIGS. 5B and 5C show experimental results comparing a bright-field measurement of a via (FIG. 5B) with a gray-field measurement of a via (FIG. 5C);

FIG. 6A exemplifies the optical system of the invention utilizing an attenuating assembly formed by a transmission pattern accommodated in a common segment of the illumination and detection channels of the optical system;

FIGS. 6B and 6C show two examples respectively of the transmission pattern; and

DETAILED DESCRIPTION OF EMBODIMENTS

Figure 3A:
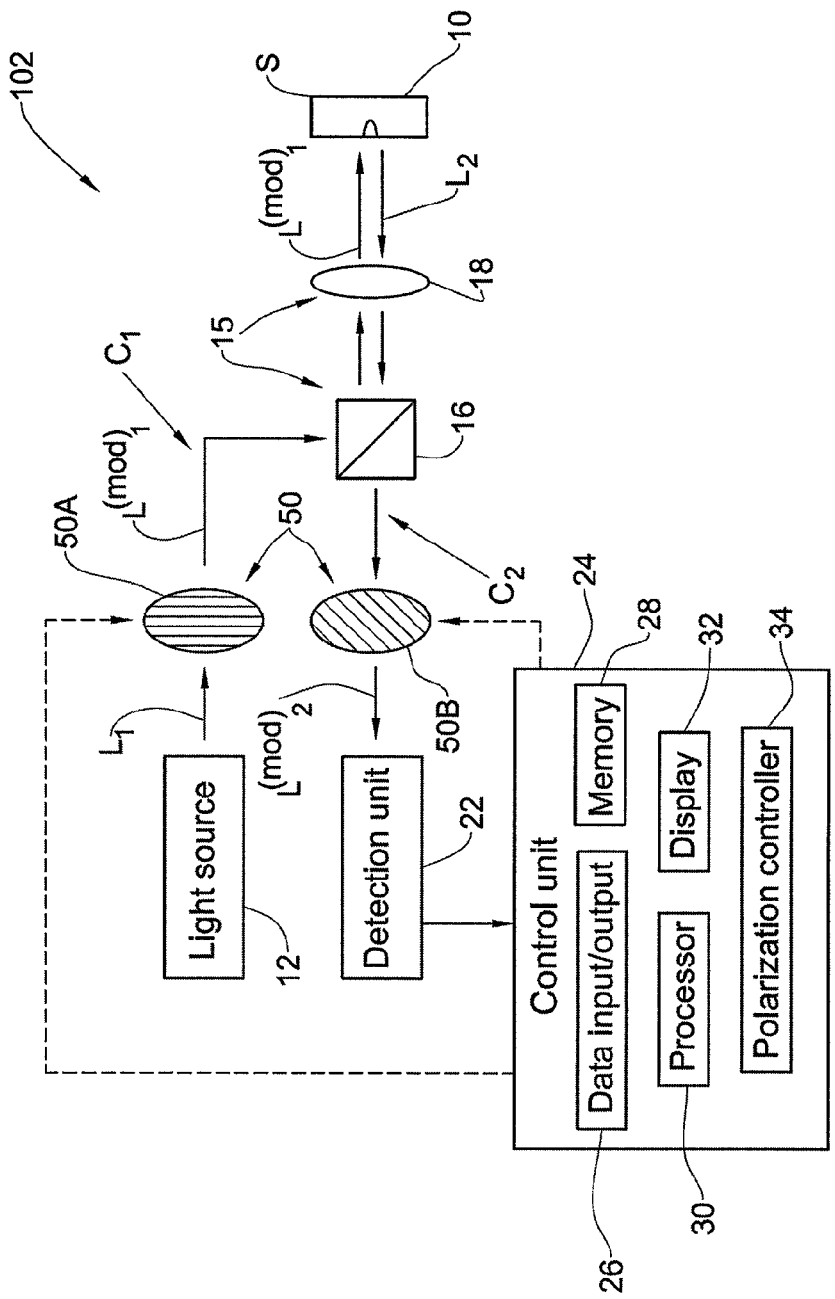
FIGS. 3A, 3B and 4 show three examples respectively of an optical system of the invention, in which an attenuating assembly is configured and operable for affecting polarization of light passing along illumination and detection channels.

FIG. 1 schematically illustrates a typical via profile defining such parameters as top diameter, bottom diameter, depth, and sidewall ripples.

As indicated above, the present invention provides for measuring/monitoring one or more of the above parameters, in particular via depth parameter utilizing a measurement mode corresponding to a combined dark and bright field detection condition for light being detected from the structure (wafer) under measurements. This combined measurement mode may be performed (initiated) selectively, as will be described further below.

FIG. 2 illustrates, by way of a block diagram, a measurement system 100 including an optical system 102 configured and operable according to the present invention to enable measuring in patterned structures (such as semiconductor wafers) having vias. The optical system 102 includes an illumination channel $C_1$ for directing illuminated light $L_1$ onto the structure being measured, a detection channel $C_2$ for collecting and directing light formed by light $L_2$ returned from the illuminated structure towards a detection unit 22, and an attenuation assembly 50. It should be noted that the illumination and detection channels $C_1$ and $C_2$ may be partially overlapping. Preferably, these channels are configured in accordance with a normal incidence mode.

It should also be noted that the detection unit 50 installed in the detection channel of the optical system 102 may be constituted by a detector (e.g. with its associated optics) or by an optical window or light guiding assembly which directs light returned from the structure towards a detector installed outside the housing of the system 100. As shown in the figure, the illumination channel includes a light source 12, which similarly may constituted by a light emitting assembly installed inside the housing of the system 100 or an optical window or guiding assembly directing light from an external light emitting assembly. The light source 12 is configured for producing broadband illumination, and the detection unit 22 comprises/is associated with a spectrometer. The detected light response of the illuminated region is thus in the form of a spectral signature.

The attenuation assembly 50 includes one or more optical assemblies/elements, two such assemblies 50A and 50B being shown in the non limiting example of FIG. 2 accommodated in the illumination and detection channels $C_1$ and $C_2$. The attenuation assembly 50 (one or more assemblies together) is adapted for attenuating light propagating along the detection channel to create a predetermined gray field condition for the light being detected. Thus, optical element(s) appropriately attenuate(s) the illuminating light $L_1$ propagating from the light source 12 along the illumination channel $C_1$, and attenuated light $L^{(mod)}_1$ is incident onto a wafer, on its via-containing region. The attenuation of the illuminating light might not necessarily include affecting of the light intensity but includes affecting an optical property of the illuminating light in order to enable selective attenuation of the returned light, as described above. Hence, the term "attenuation" when referred to the illuminating light should be interpreted properly. Thus, light $L_2$ returned from the illuminated region propagates along the detection channel $C_2$ and undergoes selective attenuation by assembly 50B. So produced attenuated light $L^{(mod)}_2$ propagates along the detection channel $C_2$ towards the detection unit 22. The attenuating assembly 50 is configured and operable to create (e.g. selectively) a predetermined combined dark and bright field detection condition for the attenuated light $L^{(mod)}_2$ propagating along the detection channel. This condition is such that the attenuated light $L^{(mod)}_2$ includes a first light portion corresponding to a dark field condition and a second light portion corresponding to a bright field condition with a predetermined relation/ratio between them. The latter corresponds to a predetermined ratio between the intensities of light returned from the via bottom and from the top surface of the wafer.

Further provided in the measurement system 100 is a control unit 24, which is connectable to the output of the detector 22 (which is exemplified in the figure as being installed in the housing of the optical system 102), via wires or wireless signal transmission, for receiving and analyzing measured data (spectral signature) indicative of the detected selectively attenuated light $L^{(mod)}_2$. The control unit 24 is typically a computer system including inter alia such functional utilities as data input and output utilities 26, memory 28, processor 30 and possibly also a display 32. The control unit 24 may also include an attenuation controller 34 in case at least one of the attenuation assemblies/elements is a tunable device for selectively adjusting the degree of attenuation, as well as may include an illumination controller 35 and/or detection controller 37.

As indicated above, the predetermined gray field detection mode may be created selectively. For example, the optical system 102 may be initially operated in either bright field detection mode or dark field detection mode or both bright and dark field detection modes (mixed mode), and be selectively, e.g. upon identifying certain condition/parameter of the structure under measurements, be shifted from that mode into the gray field detection mode. To this end, the attenuation assembly may be shiftable between its inoperative position (i.e. being outside the illumination and detection channels or being in said channels but not affecting the light propagation therethrough) into its operative position in which it affects the light passing therethrough.

The following are several examples of the configuration of the optical system 102 of the present invention. To facilitate understanding, the same reference numbers are used for identifying components that are common in all the examples. In each of these examples, the optical system defines illumination and detection channels $C_1$ and $C_2$, and is configured to create the above described combined dark and bright field detection condition for the attenuated light $L^{(mod)}_2$ being detected, i.e. a predetermined relation/ratio between the intensities of the first light portion of the detected light corresponding to a dark field condition and the second light portion of the detected light corresponding to a bright field condition.

In some embodiments of the invention, the attenuating assembly 50 is configured and operable for affecting at least polarization of light passing along the illumination and detection channels. This is illustrated in FIGS. 3A-3B and 4.

Figure 3B:
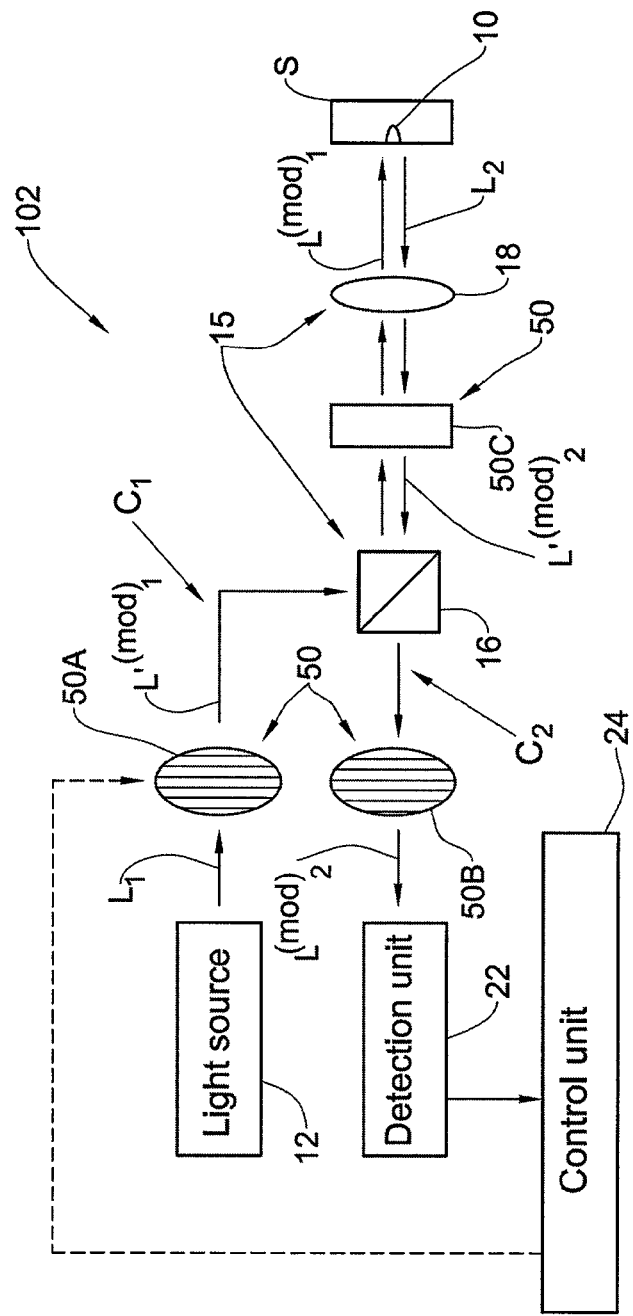
Figure 4:
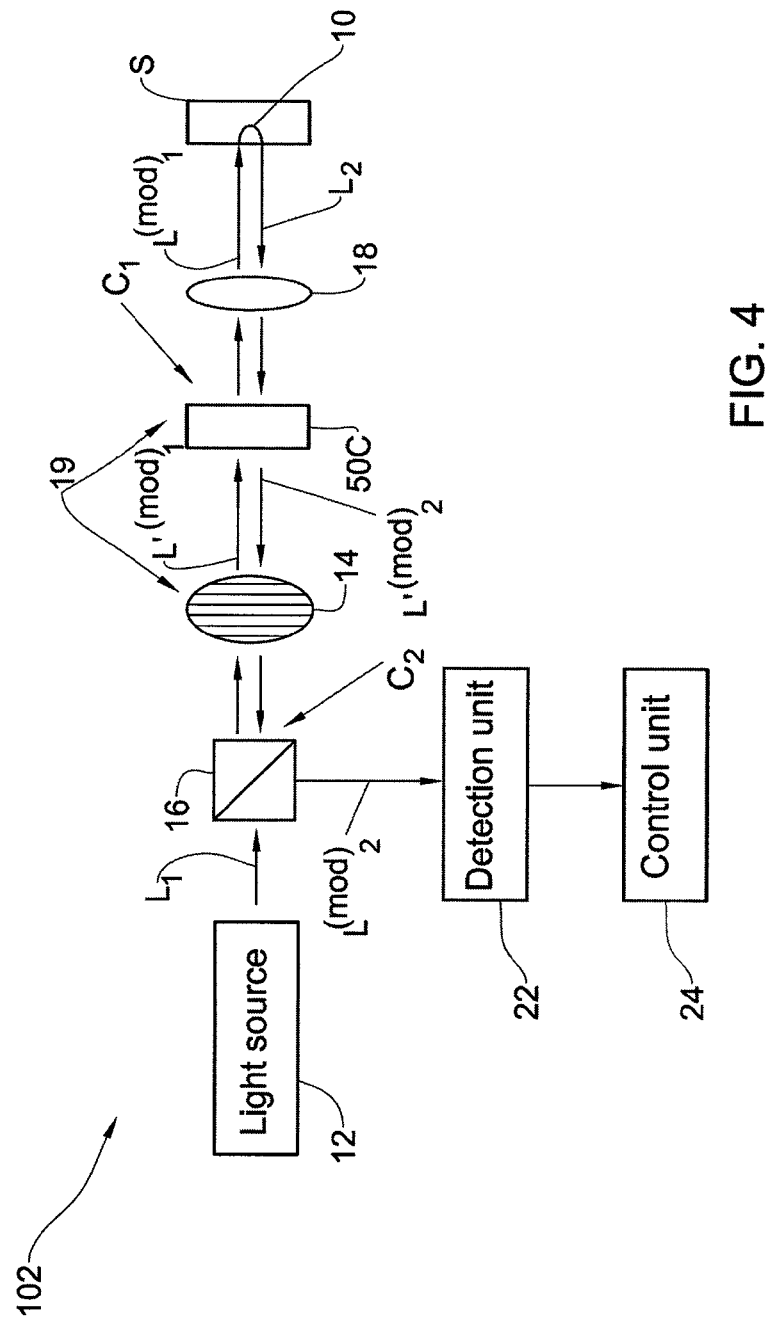

In the example of FIG. 3A, the attenuating assembly 50 includes a polarizer 50A in the illumination channel $C_1$ and an analyzer 50B in the detection channel $C_2$. The polarizer 50A affects the polarization of the illuminating light $L_1$ thus producing polarized light $L^{(mod)}_1$ incident onto the structure. The analyzer 50B has a plane of polarization oriented at a predetermined acute angle relative to that of the polarizer 50A. This acute angle has a value close to 90 degrees, for example being 70 or high degrees. This angle is preferably selected to provide that intensities of specularly reflected and scattered light portions are of the same order.

The use of selective attenuation of light by affecting its polarization is based on the following: Light specularly reflected from the wafer surface maintains its original polarization and thus after passing through the analyzer 50B, whose plane of polarization is oriented at a predetermined acute angle relative to that of the polarizer, is obstructed to some degree. However, the polarization distribution of light reflected from the via bottom is different, while the polarization distribution of light scattered from the via bottom (which is not flat) and scattered from the side walls is significantly different, so that a larger portion of light reflected from the via bottom can pass the analyzer 50B and only a small part of light returned from the side walls can pass the analyzer. As a result, a ratio between light reflected from the wafer surface and light reflected from the via bottom is properly adjusted, and the oscillatory via signal becomes stronger, as compared to the induced noise.

More specifically, referring to FIG. 3A, the system 102 includes a light source unit 12 (which may be constituted by a light emitting arrangement or by a light guiding unit associated with an external light emitter), a detection unit 22, and a light attenuating assembly 50. Also provided in the optical system is a light collecting/directing arrangement 15. In the present example, the illumination and detection channels are partially overlapping. According, the light collecting/directing arrangement 15 accommodated in a common portion of the illumination and detection channels $C_1$ and $C_2$ includes a beam splitter 16 and common focusing optics (objective) 18. Light $L_1$ coming from the light source 12 propagates along the illumination channel $C_1$, and is polarized by the polarizer 50A, and resulting polarized light $L^{(mod)}_1$ is reflected by the beam splitter 16 towards objective 18 that focuses light onto a via-containing region 10 of a structure S under measurements. Light $L_2$ reflected (returned) from the illuminated region propagates along the detection channel $C_2$ being focused by optics 18 onto the beam splitter 16 and transmitted thereby to the analyzer 50B which effects selective attenuation of light passing therethrough, as described above. The so-produced selective attenuated light $L^{(mod)}_2$ propagates to the detection unit 22.

As indicated above, the plane of polarization of analyzer 50B is oriented at a certain angle relative to the plane of polarization of polarizer 50A. Light reflected from the wafer surface maintains its polarization (a first light portion corresponding to the bright mode condition), and is thus obstructed to some degree by the analyzer 50B, while a larger portion of light reflected from the via bottom, due to the fact that its polarization distribution is somewhat different (part of a second light portion corresponding to the dark mode condition)

passes the analyzer 50B. As for the light components returned from the side walls of the via 10, they undergo significant polarization change, and thus only a small part of this light (part of the second light portion corresponding to the dark mode condition) passes through the analyzer 50B. As a result of a required ratio between the first and second light portions formed by specularly reflected and scattered light components in the attenuated light, the detected spectral signature formed by spectral distribution of the intensities of the first and second light portions is indicative of the via depth.

As shown in the example of FIG. 3B, the gray field mode (combined dark and bright field detection condition for the returned light) may optionally using in the attenuating assembly 50 a phase retarder 50C that rotates the light polarization by an appropriate angle, while polarizer 50A and analyzer 50B have substantially the same orientation of their planes of polarization. The system operates in the following manner.

Light $L_1$ from a light source 12 passes through a polarizer 50A, and polarized light $L^{(mod)'}_1$ is reflected by a beam splitter 16 onto a phase retarder 50C which rotates the light polarization by $\theta=45°$, and the so-produced light $L^{(mod)}_1$ is focused by objective $L_1$ onto the sample. Returned (reflected) light $L_2$ is focused by lens unit 18 onto the phase retarder 50C, and its phase is again rotated by 45°, resulting in light $L^{(mod)'}_2$ which then passes the polarizer 50B (which has preferred plane of polarization oriented in parallel to that of incident path polarizer 50A) located in the detection path $C_2$, resulting in selectively attenuated returned light $L^{(mod)}_2$. As described above, the light components specularly reflected from the wafer surface maintain the original polarization, while those reflected from the via bottom have somewhat different polarization, and light scattered from the side walls of the via have significantly different polarization distribution. All these light components undergo polarization rotation by the retarder and as a result the following selective attenuation applied by the analyzer 50B even more distinguish between the different light components.

A similar effect can be obtained by using an attenuation assembly 50 in the form of a single polarizer 50A installed at a point common to both illumination and collection paths $C_1$ and $C_2$, followed by a retarder 50C, as schematically illustrated in FIG. 4. Here, the retarder 50C induces a polarization rotation of light as it passes from the polarizer to the wafer and from the wafer back to the polarizer after reflection. More specifically, the polarizer 50A is located between the beam splitter 16 and the phase retarder 50C. Light $L_1$ from a light source 12 passes through a polarizer 50A, and polarized light $L^{(mod)'}_1$ is reflected by a beam splitter 16 onto a phase retarder 50C which rotates the light polarization by $\theta=45°$, and the resulting illuminating light $L^{(mod)}_1$ is focused by objective $L_1$ onto the sample. Returned (reflected) light $L_2$ is focused by lens unit 18 onto the phase retarder 50C, and its phase is again rotated by 45°, resulting in light $L^{(mod)'}_2$ which then passes the polarizer 50B (which has preferred plane of polarization oriented in parallel to that of incident path polarizer 50A) in the detection path $C_2$, resulting in selectively attenuated returned light $L^{(mod)}_2$. With this configuration, as indicated above, the retarder induces a polarization rotation of light as it passes from the polarizer to the wafer and from the wafer back to the polarizer after reflection. Specularly reflected light (light returned from the wafer surface) is thus almost suppressed, due to its rotated polarization upon return to the polarizer. In contrast, light that has its polarization rotated by the sample (via bottom and side walls) will not be similarly attenuated by the polarizer. As in the polarizer-analyzer arrangement, this setup allows control over the relative contribution of light reflected from the wafer top surface and light reflected from the via bottom.

In some embodiments of the invention, the attenuating assembly 50 is configured and operable for partial masking of both the illumination and detection channels, or in other words using gray-field angular distribution. This is schematically illustrated in FIG. 5A. This technique is based on ascertaining that for most transparent points on the mask, the conjugate points (corresponding to the location to which the ray is reflected) are opaque. As shown in FIG. 5A, the effect of the mask (constituting an attenuating assembly) associated with an objective lens 18 is such that a part 18A of the objective aperture 18 is opaque, and the other part 18B is transparent. An incoming light ray $I_1$ which is specularly reflected from a flat surface S is reflected into a point R in the opaque part 18A of the lens aperture, and is thus blocked. There is, however, a small population of rays (such as $I_2$) for which specular reflection is not blocked (because of the masking pattern configuration with respect to the light propagation channels), these rays are reflected/scattered into point R' in the transparent part 18B of the lens. Thus, rays having their propagation direction altered by the sample, as well as a small predetermined fraction of light reflected from the top surface are collected, implementing a gray field measurement. Thus, light is incident at a restricted range of angles onto the wafer surface, e.g. by partially blocking the incident light path. The collection path is also restricted, effectively blocking a significant portion of the specularly reflected light. Correspondingly, only a small fraction of light reflected from the top surface will be collected. Conversely, a larger portion of light entering the via will reach the detector, as its path is bent by the curved via bottom and via walls.

A measured example of such a comparison is presented in FIGS. 5B and 5C. FIG. 5B shows a bright-field reflectometry measurement of a via, showing fast oscillations resulting from interference between reflections from the wafer surface and from the via bottom, and FIG. 5C shows a gray field reflectometry measurement of a via, where the angular distribution of incident and collected light is restricted, reducing the contribution from light specularly reflected from the wafer surface. As a result, the contrast of the fast spectral oscillations is greatly increased in the gray-field measurement.

Gray-field angular distribution could be provided in various ways. In this connection, reference is made to FIGS. 6A to 6C exemplifying the optical system of the invention utilizing this concept. As shown in FIG. 6A, a masking element 50 (constituting an attenuating assembly) with appropriate transmission pattern is placed upstream of the focusing optics 18 with respect to the incident light propagation direction, limiting the illuminated regions on the objective and consequently the range of angles that are incident upon the wafer. Similarly, such mask partially blocks the returned light, limiting the acceptable reflected rays at the detector. More specifically, light $L_1$ from the light source 12 is directed onto the beam splitter 16, which reflects this light onto the mask 50 and attenuated light $L^{(mod)}_1$ emerging from the mask is focused by objective 18 onto the wafer. Reflected light $L_2$ is collected by objective 18 and directed onto the mask 50 again, producing attenuated returned light $L^{(mod)}_2$ which is transmitted through the beam splitter towards the detector 22. Such mask partially blocks the return path, limiting the acceptable rays after reflection.

FIG. 6B shows an example of masking element 50. The transmission pattern of the mask is such that a part of the objective aperture somewhat less than half of the aperture is rendered opaque, as described above with reference to FIG. 5A.

The mask 50 illustrated in FIG. 6B is simple for implementation but could strongly break left-right symmetry that might lead to unwanted effects. For example, such symmetry breaking may cause different sensitivity to objects oriented in the horizontal or vertical direction. Such effects may be reduced to some degree by using a mask pattern in which the field is divided into more than two parts. The specular reflection from the surface of the object is partially limited, as most transparent regions in the incident path are conjugated by masked regions at the return path. Generally, the field could be divided into 2n wedges, with n being an odd number (so that it is possible to have pairs of opposing transparent and blocked parts). This is schematically illustrated in FIG. 6C. Such designs are advantageous in terms of rotational symmetry, but may be harder to manufacture and are limited by the requirement that each transparent part is considerably wider than the wavelength, in order to avoid diffraction effects.

As indicated above, using a single mask to control the allowed light paths might result in breakage of the rotational symmetry, and might lead to unwanted artifacts. An alternative technique may be based on using separate masking of the allowed light paths in the illumination and detection channels. This is exemplified in FIG. 7 showing an optical system 102 which is configured generally similar to the above-described system of FIG. 3A but in which different polarizers in the illumination and collection paths $C_1$ and $C_2$ are replaced by different illumination and collection patterns (masks) located preferably at or near the back focal plane of the objective 18.

Figure 7:
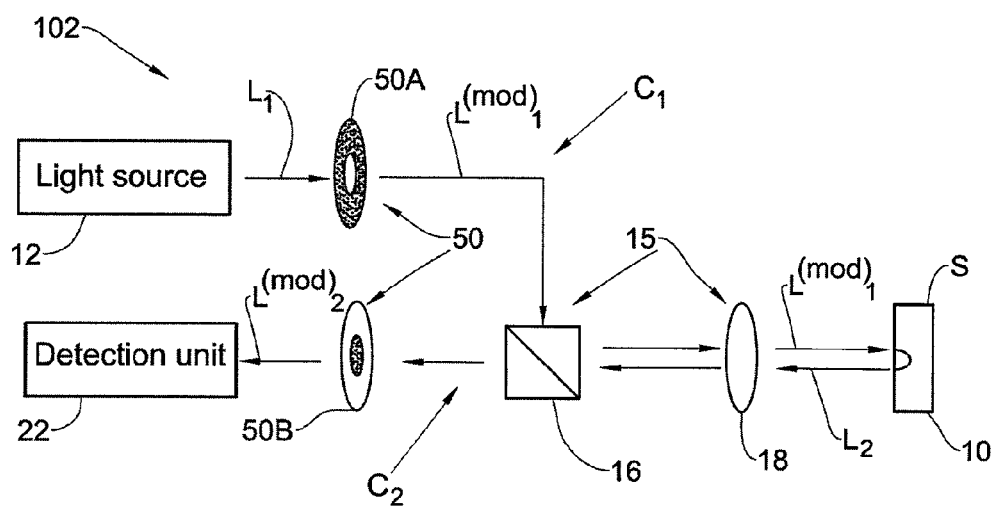
FIG. 7 exemplifies the optical system of the invention utilizing an attenuating assembly formed by two transmission patterns accommodated in respectively the illumination and detection channels of the optical system.

As shown in FIG. 7, light $L_1$ from the light source 12 passes through the illumination mask 50A, and attenuated light $L^{(mod)}_1$ transmitted through the mask 14 (mainly through the central region thereof) is directed onto the wafer S by the beam splitter 16 and objective 18. Reflected light $L_2$ from the wafer is collected by the objective 18 and transmitted by beam splitter 16 onto the collection mask 50B. Light portion $L^{(mod)}_2$ attenuated by passage through the mask (formed by light mostly transmitted through the periphery region of the mask 50B) is detected by the detector 22. In this implementation, the incident light path is partially blocked by the mask 50A, leaving a circular transparent region in the center of the field and blocking region in the periphery. A conjugate mask 50B, blocking the central circular region is used in the reflected light path $C_2$, so that light reflected from flat horizontal surfaces in the wafer is significantly attenuated (blocked) and large portion of light that was scattered by the via side walls and from curved surface of the via bottom is collected. Again, in order to reduce bright-field contribution, the masks are designed to have an overlap. Contrary to the methods based on a single mask described above, in this approach the cylindrical symmetry is maintained.

The optimal degree of extinction applied to the bright-field signal in order to get an appropriate gray field can be estimated as follows. Considering the Eq. 1 above, the best contrast for the depth-induced spectral oscillations is obtained when $A_0/A_1 \approx 1$ in Eq. 1, i.e. when the signal arising from reflection from the wafer top surface is equal to the reflection from the via bottom. As a rough estimate, let us assume light reflected from the via bottom is reflected with its polarization arbitrarily rotated. Given a large initial ratio $A_0/A_1$ for the bright-field signal, an analyzer can be used having a plane of polarization oriented with respect to that of polarizer at angle $$\alpha = a\sin(\text{sqrt}(1-A_1/A_0))$$

Light reflected from the wafer top surface experiences an extinction given by $$1-\sin^2(\alpha)=A_1/A_0,$$

while light reflected from the via bottom goes through no (or at least much smaller) extinction. As a result, the eventual relative reflection strength of these two components is made similar, leading to greatly improved visibility of the oscillations. For example, if the bright-field oscillations have typical contrast of 5%, the plane of polarization of the analyzer can be rotated to an angle of $\alpha \approx 77°$. Usually, observed bright-field oscillations have typical contrast in the range 1-10%.

This principle can be applied to estimate the degree of restriction applied to the angular distribution of rays. Assuming the via reflects light in significantly broadened span of directions, it will be much less sensitive to the blockage of the allowed reflected directions. As described above, in this case there are two distinct groups of incidence directions: for some range $\Omega$ of incidence directions, specular reflection is collected by the detector. However, for the remaining incidence directions $(1-\Omega)$, such reflection paths are almost blocked. While the first group of rays contributes to reflection from both the wafer surface and the via bottom, rays for which specular reflection is significantly attenuated only contribute to signal arising from the side walls of the via. Hence, $\Omega$ is optimized for via depth detection when $\Omega/(1-\Omega) \approx A_1/A_0$.

Thus, the present invention provides a novel effective technique for determining the via depth, by selectively attenuating light in the detection channel in an optical system by affecting one or more properties of incident and returned light to create an effective gray field detection mode. Regular spectrum (intensity vs wavelength) can be transformed into wavenumber spectrum, because periodic oscillations appear solely in wavenumber spectrum. The strong fast oscillations in the wavenumber spectrum correspond to interference signal/pattern formed by light returned from the via bottom and the wafer top surface.

One way of quantifying the visibility of such oscillations is through spectral analysis of the measured data (spectral signature). Such analysis provides a quantitative measure for the existence of typical frequencies in the spectral signature. A very common tool for such analysis is the Fourier transform, where oscillations give rise to a distinct sharp peak at the Fourier spectrogram. The position of this peak is determined by the frequency of oscillations, which (as stated) is determined by the TSV depth.

It should be understood that the method of quantifying the visibility of the fast oscillations using a Fourier transform is an example and many other known methods of spectral analysis can be used as well. These include inter alia such techniques as the Pisarenko and MUSIC algorithms for harmonic decomposition, the Welch, Yule-Walker and Burg algorithms, the eigenvector spectral decomposition and many more. The principles of these techniques are known per se and therefore need be described in details. Any such method can be used to identify and quantify the existence of a fast frequency in the measured signal, corresponding to a value consistent with the via depth. It should also be understood that rough estimate of the via depth is sufficient in order to identify the reasonable range at which such frequency is expected.

The invention claimed is:

1. An optical system for use in measuring in patterned structures having vias, the system comprising:
   an illumination channel for propagating illuminated light onto the structure being measured,
   a detection channel for collecting light returned from the illuminated structure to a detection unit, and an attenuation assembly accommodated in the illumination and detection channels and being configured and operable for selectively attenuating light propagating along the detection channel, the attenuation creating a predetermined condition for the selectively attenuated light, said predetermined condition being defined by a predetermined ratio between a first light portion corresponding to a dark field condition and a second light portion corresponding to a bright field condition in said selectively attenuated light, detected selectively attenuated light being therefore indicative of at least one parameter of the via being illuminated.

2. The system of claim 1, wherein the first and second light portions correspond to respectively substantially scattered light and substantially specularly reflected light.

3. The system of claim 1, wherein the illuminating channel comprises a broadband light source, and the detection channel comprises a spectrometer, the detected light being in the form of a spectral signature.

4. The system of claim 1, wherein said spectral signature is indicative of at least a depth of the via being illuminated.

5. The system of claim 1, wherein the illumination and detection channels are configured in accordance with a normal incidence mode.

6. The system of claim 1, wherein the attenuating assembly is configured and operable for affecting at least polarization of light passing along the illumination and detection channels.

7. The system of claim 6, wherein the attenuating assembly comprises first and second polarizers accommodated in the illumination and detection channels and having planes of polarization forming a predetermined acute angle between them.

8. The system of claim 7, wherein said predetermined acute angle is higher than 70 degrees.

9. The system of claim 7, wherein said predetermined acute angle is selected such that intensities of the first and second light portions are of the same order.

10. The system of claim 7, wherein the attenuating assembly comprises:
first and second polarizers accommodated in the illumination and detection channels respectively and having planes of polarization oriented to form said predetermined acute angle, and
a common phase retarder accommodated in the illumination and detection channels, and being located upstream of the second polarizer with respect to a direction of propagation of light returned from the structure along the detection channel.

11. The system of claim 7, wherein the attenuating assembly comprises a common polarizer and a common phase retarder both accommodated in a spaced-apart relationship in a common portion of the illumination and detection channels, the polarizer being located upstream of the phase retarder with respect to a direction of propagation of the illuminating light to the structure along the illumination channel.

12. The system of claim 1, wherein the attenuating assembly is configured and operable for partial masking of both the illumination and detection channels.

13. The system of claim 12, wherein the attenuating assembly comprises a mask with a predetermined transmission pattern, the transmission pattern being configured to provide said predetermined ratio between the intensities of the first and second light portions, said mask being located in a plane intersecting the illumination and detection channels.

14. The system of claim 13, wherein said mask has at least two segments of different transmissions with respect to the first and second light portions.

15. The system of claim 13, wherein the attenuating assembly comprises first and second masks having complementary patterns, each pattern being formed by regions of different light transmission with respect to the first and second light portions.

16. The system of claim 1, comprising a control unit configured and operable for receiving measured data indicative of the selectively attenuated light in the detection channel, and processing said measured data to determine at least one parameter of the via.

17. The system of claim 3, comprising a control unit configured and operable for receiving the measured data indicative of the spectral signature corresponding to the selectively attenuated light in the detection channel, and processing said measured data to determine at least one parameter of the via.

18. The system of claim 1, comprising a control unit configured and operable for selectively operating the attenuating assembly for selectively shifting it into an operative mode corresponding to said predetermined condition.

19. The system of claim 18, wherein said control unit is configured and operable to selectively operate the attenuating assembly in either one of the following additional modes: a bright field detection mode, a dark field detection mode, and intermediate mixed dark and bright field detection modes.

20. A method for use in optical measurements in patterned structures having vias, the method comprising selectively attenuating light returned from an illuminated via-including region, the selective attenuation creating a predetermined combined dark and bright field detection condition, such that said selectively attenuated returned light comprises a first light portion corresponding to a dark field condition and a second light portion corresponding to a bright field condition, with a predetermined ratio between intensities of the first and second light portions, the selectively attenuated light being therefore indicative of at least one parameter of the via being illuminated.

21. The method of claim 20, wherein said illuminating light is produced by a broadband light source, said attenuated returned light being in the form of a spectral signature.

22. The method of claim 20, wherein said at least one parameter of the via comprises at least a via depth.

23. The method of claim 20, wherein said predetermined combined dark and bright field detection condition is selectively created.

24. The method of claim 20, wherein said selective attenuations comprises affecting at least polarization of light passing along the illumination and detection channels.

25. The method of claim 20, wherein said selective attenuations comprises partial masking of both the illumination and detection channels.

26. The method of claim 21, comprising receiving and processing the measured data corresponding to the spectral signature of the detected attenuated light, and determining at least one parameter of the via.

27. A method for use in optical measurements in patterned structures having vias, the method comprising: providing an optical system configured and operable for performing optical measurements with a bright field detection mode and a dark field detection mode, and selectively operating said optical system for applying an attenuation mode for selectively attenuating light returned from an illuminated via-including region, the attenuation being adapted to create a predetermined combined dark and bright field detection condition for said attenuated returned light, such that the attenuated returned light comprises a first light portion corresponding to a dark field condition and a second light portion corresponding to a bright field condition, with a predetermined ratio between intensities of the first and second light portions, the attenuated returned light being therefore indicative of at least one parameter of the via being illuminated.

\* \* \* \* \*